(12) United States Patent
Verma et al.

(10) Patent No.: US 10,632,254 B2
(45) Date of Patent: Apr. 28, 2020

(54) METHOD AND APPARATUS FOR WETTING INTERNAL FLUID PATH SURFACES OF A FLUID PORT TO INCREASE ULTRASONIC SIGNAL TRANSMISSION

(71) Applicant: Becton, Dickinson and Company, Franklin Lakes, NJ (US)

(72) Inventors: Kaushal Verma, Somerset, NJ (US); Brandi Ford, Apex, NC (US); Shawn Wayne DeKalb, San Diego, CA (US); Hong Zhu, Glen Rock, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/293,929

(22) Filed: Mar. 6, 2019

(65) Prior Publication Data
US 2019/0201621 A1    Jul. 4, 2019

Related U.S. Application Data

(63) Continuation of application No. 15/626,510, filed on Jun. 19, 2017, now Pat. No. 10,258,742.
(Continued)

(51) Int. Cl.
| | | |
|---|---|---|
| *A61M 5/168* | (2006.01) | |
| *A61M 5/14* | (2006.01) | |
| *A61M 5/172* | (2006.01) | |
| *G01F 1/66* | (2006.01) | |
| *A61M 5/145* | (2006.01) | |

(Continued)

(52) U.S. Cl.
CPC ...... *A61M 5/16886* (2013.01); *A61M 5/1452* (2013.01); *A61M 5/16877* (2013.01); *A61M 5/172* (2013.01); *A61M 39/10* (2013.01); *G01F 1/662* (2013.01); *A61M 5/141* (2013.01); *A61M 2005/1402* (2013.01);
(Continued)

(58) Field of Classification Search
CPC ............. A61M 5/16; A61M 5/14; A61M 5/17
See application file for complete search history.

(56) References Cited

U.S. PATENT DOCUMENTS

| | | |
|---|---|---|
| 3,144,769 A | 8/1964 | Francisco, Jr. |
| 3,528,288 A | 9/1970 | Scourtes |

(Continued)

FOREIGN PATENT DOCUMENTS

| | | |
|---|---|---|
| EP | 2857803 A1 | 4/2014 |
| WO | 0209795 A2 | 2/2002 |

(Continued)

*Primary Examiner* — Jewel V Dowtin
(74) *Attorney, Agent, or Firm* — The Webb Law Firm

(57) ABSTRACT

A method for readying a fluid sensor associated with a medical device includes attaching a flow restrictor to a fluid outlet of the fluid sensor. The fluid sensor includes a fluid channel, a fluid inlet at a first end of the fluid channel configured to couple to an outlet of an administrable fluid source, and the fluid outlet at a second end of the fluid channel. Fluid is delivered from the administrable fluid source to the fluid channel through the fluid inlet. A syringe actuation device including a force limiting device may be used to deliver the fluid. The fluid is pressurized in the fluid channel between the fluid inlet and the flow restrictor to wet an interior surface of the fluid channel with the fluid. The flow restrictor is removed from the fluid outlet.

21 Claims, 9 Drawing Sheets

Related U.S. Application Data

(60) Provisional application No. 62/351,459, filed on Jun. 17, 2016.

(51) Int. Cl.
*A61M 39/10* (2006.01)
*A61M 5/31* (2006.01)

(52) U.S. Cl.
CPC ............... *A61M 2005/3123* (2013.01); *A61M 2205/3331* (2013.01); *A61M 2205/3375* (2013.01)

(56) References Cited

U.S. PATENT DOCUMENTS

| | | | |
|---|---|---|---|
| 4,299,336 A | 11/1981 | Studer | |
| 4,352,459 A | 10/1982 | Berger et al. | |
| 4,398,428 A | 8/1983 | Kato | |
| 4,474,180 A | 10/1984 | Angulo | |
| 4,561,438 A | 12/1985 | Bonnet et al. | |
| 4,599,082 A * | 7/1986 | Grimard | A61M 5/284 215/355 |
| 4,677,858 A | 7/1987 | Ohnhaus | |
| 4,788,869 A | 12/1988 | Li | |
| 5,048,798 A | 9/1991 | Araki et al. | |
| 5,221,282 A | 6/1993 | Wuchinich | |
| 5,279,163 A | 1/1994 | D'Antonio et al. | |
| 5,463,906 A | 11/1995 | Spani et al. | |
| 5,496,285 A * | 3/1996 | Schumacher | A61M 5/31511 604/218 |
| 6,155,463 A | 12/2000 | Dentler | |
| 6,435,030 B1 | 8/2002 | Gysling et al. | |
| 6,619,139 B2 | 9/2003 | Popp | |
| 6,981,960 B2 | 1/2006 | Cho et al. | |
| 7,018,360 B2 | 3/2006 | Flaherty et al. | |
| 7,032,435 B2 | 4/2006 | Hassenflug | |
| 7,255,006 B2 | 8/2007 | Spanke et al. | |
| 7,264,885 B2 | 9/2007 | Rosen et al. | |
| 7,560,494 B2 | 7/2009 | Steinbrenner et al. | |
| 7,762,988 B1 | 7/2010 | Vitello | |
| 7,782,202 B2 | 8/2010 | Downie et al. | |
| 7,882,751 B2 | 2/2011 | Hoecker | |
| 7,976,508 B2 | 7/2011 | Hoag | |
| 8,544,344 B2 | 10/2013 | Murakami | |
| 8,714,030 B1 | 5/2014 | Liu et al. | |
| 8,863,589 B2 | 10/2014 | Bitto et al. | |
| 8,904,878 B2 | 12/2014 | Wiest et al. | |
| 9,320,493 B2 | 4/2016 | Visveshwara | |
| 9,541,431 B2 | 1/2017 | Nakano et al. | |
| 9,586,013 B2 | 3/2017 | Bai | |
| 9,833,575 B2 * | 12/2017 | Manke | A61M 5/31511 |
| 9,884,152 B2 | 2/2018 | McLoughlin et al. | |
| 9,981,086 B2 | 5/2018 | Cowe et al. | |
| 2007/0034016 A1 | 2/2007 | Maginnis et al. | |
| 2007/0186684 A1 | 8/2007 | Pham | |
| 2009/0157040 A1 | 6/2009 | Jacobson et al. | |
| 2009/0204005 A1 | 8/2009 | Keast et al. | |
| 2009/0234323 A1 | 9/2009 | Bunch et al. | |
| 2009/0264768 A1 | 10/2009 | Courtney et al. | |
| 2009/0270844 A1 | 10/2009 | Seeley et al. | |
| 2010/0063765 A1 | 3/2010 | Carlisle et al. | |
| 2010/0237254 A1 | 9/2010 | Mason et al. | |
| 2011/0046514 A1 | 2/2011 | Greenwald et al. | |
| 2013/0177455 A1 | 7/2013 | Kamen et al. | |
| 2014/0033827 A1 | 2/2014 | Satou et al. | |
| 2015/0204705 A1 | 7/2015 | Forster et al. | |
| 2015/0211904 A1 | 7/2015 | Forster | |
| 2016/0084689 A1 | 3/2016 | Smith et al. | |
| 2016/0375449 A1 | 12/2016 | Cao et al. | |
| 2017/0059374 A1 | 3/2017 | DeKalb et al. | |
| 2017/0059375 A1 | 3/2017 | DeKalb | |
| 2017/0059377 A1 | 3/2017 | DeKalb | |
| 2017/0361017 A1 | 12/2017 | Verma et al. | |

FOREIGN PATENT DOCUMENTS

| | | |
|---|---|---|
| WO | 2011126895 A2 | 10/2011 |
| WO | 2014016315 A1 | 1/2014 |
| WO | 2014016316 A1 | 1/2014 |

* cited by examiner

METHOD AND APPARATUS FOR WETTING INTERNAL FLUID PATH SURFACES OF A FLUID PORT TO INCREASE ULTRASONIC SIGNAL TRANSMISSION

CROSS REFERENCE TO RELATED APPLICATIONS

The present application is a continuation of U.S. patent application Ser. No. 15/626,510 filed Jun. 19, 2017, which claims priority to U.S. provisional patent application Ser. No. 62/351,459 filed Jun. 17, 2016, the entire disclosures of which are herein incorporated by reference.

BACKGROUND OF THE INVENTION

1. Field of the Disclosure

The present disclosure relates generally to a flow sensor system. More particularly, the present disclosure relates to a flow sensor system and a method of readying a flow sensor of the flow sensor system for characterizing at least one attribute of a fluid to be detected by the flow sensor.

2. Description of the Related Art

There is a need to improve volume accuracy in a bolus delivery using a medical device. It would be advantageous to provide a flow sensor system having a flow sensor with improved flow measurement characteristics.

Signal strength is a function of acoustic energy propagation from a source through a boundary layer of air (and/or contaminants) that attenuate this propagation. As a sensor is first subjected to a fluid, a boundary is initially formed. Over time this layer begins to break down leaving micro-bubbles of air at the surface of the sensor. Micro-bubbles remain at the surface as a function of two theories: i) the partial pressure of air dissolved in the fluid and ii) the surface energy or capillary forces of a micro-bubble with respect to the surface. Lower pressure fluids contain a smaller partial pressure of air and may permit the absorption of air into the fluid. Higher pressure applied to the fluid can both shrink the bubbles and permit more surface area in contact with the fluid and, upon release, permit a detachment of the micro-bubbles to absorb into the fluid. Based on the surface topology or asperity density, micro-bubbles become lodged into cavities of the surface by capillary action or surface tension that is higher than floating in the fluid itself.

Accordingly, there is a need in the art for an improved method and apparatus for wetting internal fluid path surfaces of a fluid port to increase ultrasonic signal transmission.

SUMMARY OF THE INVENTION

The present disclosure provides a system for sensing a flow of a fluidic medicament. The system includes an intelligent injection port which may attach to an injection site (such as a "Y Site" or a stop cock) for manually administered IV injections. The system includes two main sub-assemblies: a single-use flow sensor and a reusable base unit, which fit together prior to use. The single-use flow sensor includes a flow tube sub-assembly. The present disclosure provides a method for readying the flow sensor for characterizing at least one attribute of the fluid flowing through the flow tube sub-assembly.

According to a non-limiting embodiment or aspect, provided is a method for readying a fluid sensor associated with a medical device, the method comprising: attaching a flow restrictor to a fluid outlet of the fluid sensor, the fluid sensor comprising: a fluid channel, a fluid inlet at a first end of the fluid channel configured to couple to an outlet of an administrable fluid source, and the fluid outlet at a second end of the fluid channel; delivering fluid from the administrable fluid source to the fluid channel through the fluid inlet; pressurizing the fluid in the fluid channel between the fluid inlet and the flow restrictor to wet an interior surface of the fluid channel with the fluid; and removing the flow restrictor from the fluid outlet.

In one non-limiting embodiment or aspect, the method further comprises applying a pressure to the fluid in the fluid channel between the fluid inlet and the flow restrictor over a first period of time.

In one non-limiting embodiment or aspect, the administrable fluid source comprises a syringe including a plunger, wherein the method further comprises: attaching a syringe actuation device to the syringe; and applying, with the syringe actuation device, a force to the plunger of the syringe.

In one non-limiting embodiment or aspect, the method further comprises adjusting the syringe actuation device to a first position, wherein, when in the first position, the syringe actuation device applies the force to the plunger of the syringe.

In one non-limiting embodiment or aspect, the pressure is a constant positive pressure.

In one non-limiting embodiment or aspect, the pressure is a constant negative pressure.

In one non-limiting embodiment or aspect, the method further comprises applying a constant pressure to the fluid in the fluid channel between the fluid inlet and the flow restrictor over a second period of time that is one of before the first period of time and after the first period of time.

In one non-limiting embodiment or aspect, the administrable fluid source comprises a syringe including a plunger, the method further comprising: attaching a syringe actuation device to the syringe; adjusting the syringe actuation device to a first position, wherein, when in the first position, the syringe actuation device applies a first constant force to the plunger of the syringe that applies the constant negative pressure to the fluid in the fluid channel over the first period of time; and adjusting the syringe actuation device to a second position, wherein, when in the second position, the syringe actuation device applies a second constant force to the plunger of the syringe that applies the constant positive pressure to the fluid in the fluid channel over the second period of time.

In one non-limiting embodiment or aspect, the method further comprises creating a bi-directional flow of the fluid in the fluid channel between the fluid inlet and the flow restrictor.

In one non-limiting embodiment or aspect, the method further comprises applying a varying pressure to the fluid in the fluid channel between the fluid inlet and the flow restrictor.

In one non-limiting embodiment or aspect, the flow restrictor comprises an outlet having an inner diameter that changes in response to the varying pressure applied to the fluid in the fluid channel, thereby creating a perturbative flow of the fluid in the fluid channel.

In one non-limiting embodiment or aspect, the flow restrictor comprises an elastomeric material.

In one non-limiting embodiment or aspect, the administrable fluid source comprises a syringe having a plunger, wherein the method further comprises: mounting the syringe vertically in a syringe holder; and applying a load to the plunger of the syringe.

In one non-limiting embodiment or aspect, the method further comprises shaking or vibrating the fluid sensor when the fluid is within the fluid channel.

In one non-limiting embodiment or aspect, the fluid sensor further comprises at least one piezo element, wherein the method further comprises: activating the at least one piezo element when the fluid is within the fluid channel, thereby dislodging micro-bubbles from inner walls of the fluid channel.

In one non-limiting embodiment or aspect, the method further comprises wetting the fluid channel with at least one surfactant.

In one non-limiting embodiment or aspect, the method further comprises processing at least one component of the fluid sensor using at least one of plasma etching, abrasive polishing, reaming, or any combination thereof to reduce surface roughness of the at least one component.

In one non-limiting embodiment or aspect, the method further comprises applying a negative pressure to the fluid in the administrable fluid source before delivering the fluid from the administrable fluid source to the fluid channel through the fluid inlet, thereby removing gas from the fluid.

In one non-limiting embodiment or aspect, the method further comprises attaching a suction cup to the fluid inlet; and actuating the suction cup to apply the negative pressure to the fluid in the administrable fluid source.

In one non-limiting embodiment or aspect, the method further comprises attaching a flow director between the fluid inlet at the first end of the fluid channel and the outlet of the administrable fluid source, wherein the flow director creates a spiral fluid flow in the fluid delivered from the administrable fluid source to the fluid channel through the fluid inlet.

In one non-limiting embodiment or aspect, the method further comprises heating the fluid when the fluid is within the fluid channel.

In one non-limiting embodiment or aspect, the method further comprises varying a flow rate of the fluid delivered from the administrable fluid source to the fluid channel through the fluid inlet.

In one non-limiting embodiment or aspect, the delivering the fluid from the administrable fluid source to the fluid channel through the fluid inlet comprises delivering boluses of the fluid from the administrable fluid source to the fluid channel through the fluid inlet.

In one non-limiting embodiment or aspect, the boluses are periodically delivered to the fluid channel.

In one non-limiting embodiment or aspect, the method further comprises varying at least one of the following: a volume of the boluses, a pressure applied to the fluid of the boluses, a period of time over which the pressure is applied to the fluid of the boluses, or any combination thereof.

In one non-limiting embodiment or aspect, the administrable fluid source comprises a syringe including a plunger, and wherein the method further comprises: attaching a force limiting device to the syringe; and inhibiting, with the force limiting device, an application of a pressure to the fluid in the fluid channel that violates a threshold pressure.

In one non-limiting embodiment or aspect, the force limiting device inhibits movement of the plunger of the syringe in response to the application of the pressure to the fluid in the fluid channel that violates the pressure threshold.

In one non-limiting embodiment or aspect, the administrable fluid source comprises a syringe including a plunger, and wherein the method further comprises: attaching a force limiting device to the syringe, the force limiting device including at least one pressure indicator; and indicating, with the at least pressure indicator, a current pressure applied to the fluid in the fluid channel.

In one non-limiting embodiment or aspect, said flow restrictor further comprises an outlet of approximately 34 G (0.0826 mm ID).

According to a non-limiting embodiment or aspect, provided is a method for readying a fluidic conduit associated with a medical device, the method comprising: attaching a flow restrictor to a fluid outlet of the fluidic conduit, the fluid conduit comprising: a fluid channel, a fluid inlet at a first end of the fluid channel configured to couple to an outlet of an administrable fluid source, and the fluid outlet at a second end of the fluid channel; delivering fluid from the administrable fluid source to the fluid channel through the fluid inlet; pressurizing the fluid in the fluid channel between the fluid inlet and the flow restrictor to wet an interior surface of the fluid channel with the fluid, thereby removing air bubbles from the pressurized fluid in the fluidic conduit; and removing the flow restrictor from the fluid outlet.

According to a non-limiting embodiment or aspect, provided is a method for readying a fluid sensor associated with a medical device comprising: generating a first signal by at least one sensor of a fluid port characterizing at least one attribute of a fluid within an administrable fluid source, the fluid port comprising: a fluid channel, a fluid inlet at a first end of the fluid channel configured to couple to an outlet of an administrable fluid source, and a fluid outlet at a second end of the fluid channel having a flow restrictor; removing the flow restrictor; attaching the fluid outlet at a second end of the fluid channel to an inlet configured to deliver fluid from the administrable fluid source to a fluid pathway that provides fluid to said medical device; generating a second signal of the same type as said first signal by at least one sensor of a fluid port characterizing at least one attribute of fluid, wherein said second signal is increased over the first signal.

According to a non-limiting embodiment or aspect, provided is an apparatus for controlling a plunger of a syringe to deliver a fluid from an interior of the syringe, comprising: an actuator rod extending from a proximal end to a distal end; a plunger engagement portion engaged with the distal end of the actuator rod and configured to engage the plunger of the syringe; a body having a proximal end, a distal end, and an opening at the proximal end, wherein the opening receives the plunger engagement portion, and wherein the plunger engagement portion is threadably engaged with the body.

In one non-limiting embodiment or aspect, the plunger engagement portion is configured to inhibit an application of a force to the plunger of the syringe that violates a threshold force.

In one non-limiting embodiment or aspect, the plunger engagement portion inhibits movement of the plunger of the syringe in response to a plunger reaction force applied by the plunger of the syringe.

In one non-limiting embodiment or aspect, the apparatus further comprises a clutch that engages the distal end of the actuator rod to the plunger engagement portion.

In one non-limiting embodiment or aspect, the apparatus further comprises a spring that extends within the actuator rod.

In one non-limiting embodiment or aspect, the spring extends within the actuator rod and into the plunger engagement portion via an opening in a proximal end of the plunger engagement portion, and wherein the spring engages an inner wall at the distal end of the plunger engagement portion.

In one non-limiting embodiment or aspect, an outer wall at the distal end of the plunger engagement portion engages the plunger.

In one non-limiting embodiment or aspect, the actuator rod extends into the plunger engagement portion, wherein a portion of the actuator rod that extends within the plunger engagement portion includes a radially extending flange, and wherein the clutch connects a proximal face of the flange to the inner wall at the proximal end of the plunger engagement portion.

In one non-limiting embodiment or aspect, the clutch disengages the distal end of the actuator rod from the plunger engagement section in response to a compression of the spring.

In one non-limiting embodiment or aspect, the spring compresses in response to a plunger reaction force applied by the plunger of the syringe to the plunger engagement portion.

In one non-limiting embodiment or aspect, the distal end of the body is configured to connect to the syringe, and wherein the plunger of the syringe extends within the body.

According to a non-limiting embodiment or aspect, provided is an apparatus for controlling a plunger of a syringe for delivering a fluid from an interior of the syringe, the device comprising: a handle and a cooperating trigger, wherein the trigger comprises a first portion connected to a second portion by a joint; and a spring connecting the first portion to the second portion; wherein the first portion of the trigger is configured to engage the plunger of the syringe and receive a plunger reaction force applied by the plunger of the syringe, wherein movement of the second portion of the trigger toward the handle applies a stretching force to the spring in response to the plunger reaction force, and wherein the first portion of the trigger disengages the plunger of the syringe in response to the stretching force greater than a threshold force applied to the spring.

In one non-limiting embodiment or aspect, the handle and the cooperating trigger operate one of a spring biased grip drive and a ratchet driven grip drive.

In one non-limiting embodiment or aspect, the first portion of the trigger engages the plunger of the syringe via at least one of a piston and a drive grip, and wherein the first portion of the trigger breaks the engagement with the at least one of the piston and the drive grip in response to the stretching force greater than the threshold force applied to the spring.

According to a non-limiting embodiment or aspect, provided is an apparatus for controlling a plunger of a syringe for delivering a fluid from an interior of the syringe, the device comprising: an actuator rod extending from a proximal end to a distal end; a spring extending within the actuator rod, wherein a distal end of the spring is configured to engage the plunger of the syringe; a body having a proximal end, a distal end, and an opening at the proximal end, wherein the opening receives the distal end of the actuator rod, and wherein the actuator rod comprises at least one indicator that indicates a desired amount of compression of the spring.

In one non-limiting embodiment or aspect, an outer wall of the actuator rod is in ratcheting engagement with an inner wall of the body.

In one non-limiting embodiment or aspect, a distal end of the actuator rod comprises a radially extending pawl, and wherein the inner wall of the body comprises a plurality of teeth.

In one non-limiting embodiment or aspect, at least a portion of the actuator rod and at least a portion of the body are transparent such that the spring and the plunger are visible through the actuator rod and the body.

In one non-limiting embodiment or aspect, a location of the at least one indicator with respect to a location of at least one of a distal end of the spring and a proximal end of the plunger indicates the desired amount of compression of the spring.

In one non-limiting embodiment or aspect, the actuator rod comprises at least two indicators spaced apart from one another, and wherein a location of the at least one of the distal end of the spring and the proximal end of the plunger between the at least two indicators indicates the desired amount of compression of the spring.

In one non-limiting embodiment or aspect, the distal end of the body is configured to connect to the syringe, wherein the plunger of the syringe extends within the body.

BRIEF DESCRIPTION OF THE DRAWINGS

The above-mentioned and other features and advantages of this disclosure, and the manner of attaining them, will become more apparent and the disclosure itself will be better understood by reference to the following descriptions of examples of the disclosure taken in conjunction with the accompanying drawings, wherein.

Corresponding reference characters indicate corresponding parts throughout the several views. The exemplifications set out herein illustrate exemplary examples of the disclosure, and such exemplifications are not to be construed as limiting the scope of the disclosure in any manner.

DETAILED DESCRIPTION

Figure 1:
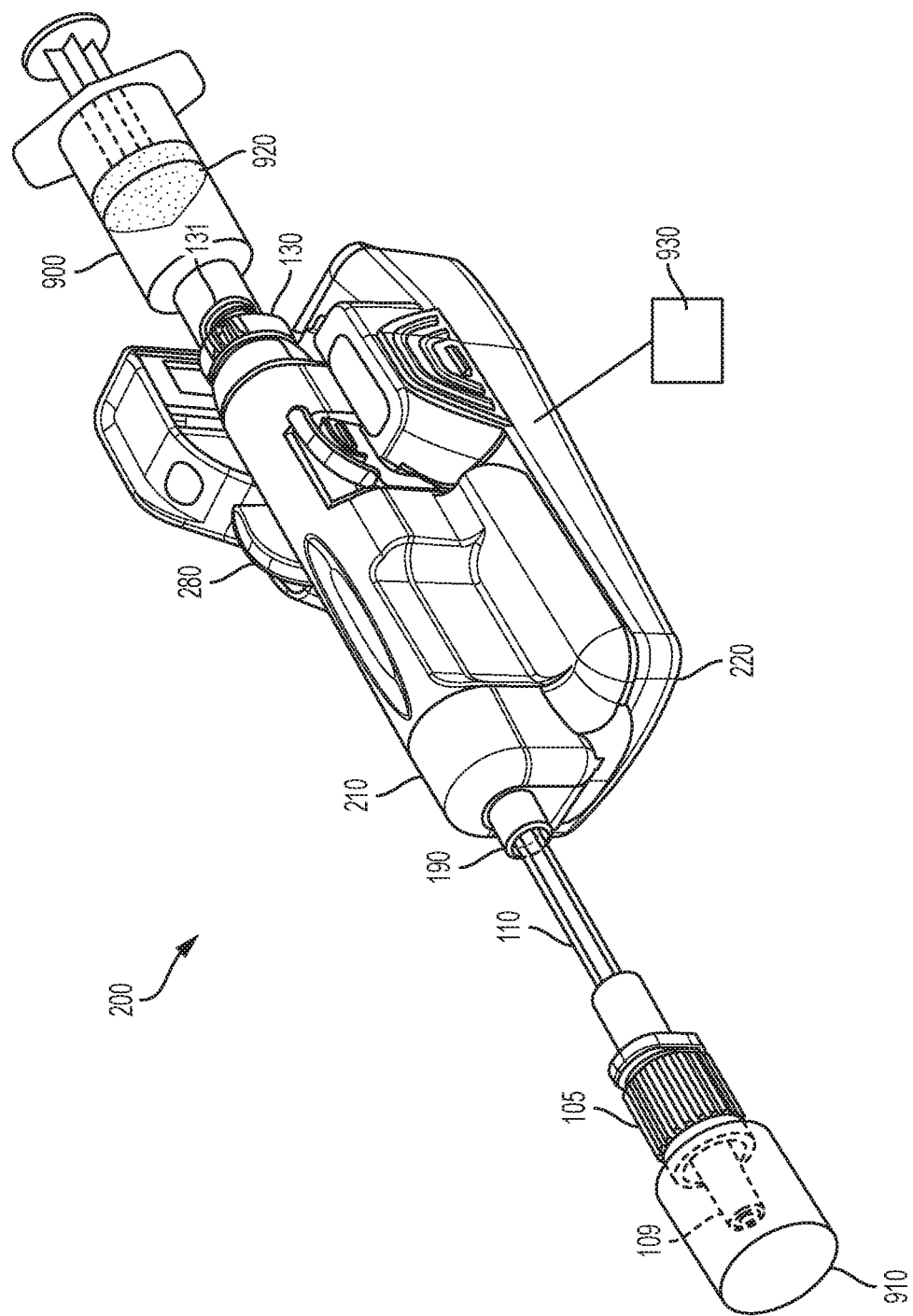
FIG. 1 is a distally-directed perspective view of a flow sensor system in accordance with one example of the present invention.

The following description is provided to enable those skilled in the art to make and use the described examples contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary.

As used in the specification and the claims, the singular form of "a", "an", and "the" include plural referents unless the context clearly dictates otherwise.

As used herein, "proximal" shall refer to a part or direction located away or furthest from a patient (upstream), while distal shall refer to a part or direction towards or located nearest to a patient (downstream). Also, a drug substance is used herein in an illustrative, non-limiting manner to refer to any substance injectable into the body of a patient for any purpose. Reference to a patient may be to any being, human or animal. Reference to a clinician may be to any person or thing giving treatment, e.g., a nurse, doctor, machine intelligence, caregiver, or even self-treatment.

As used herein, the phrase "inherently hydrophobic" refers to a surface that naturally excludes water molecules rather than by a process of drying, such as drying by hot air.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

Unless otherwise indicated, all numbers expressing quantities used in the specification and/or claims are to be understood as modified in all instances by the term "about."

Flow Sensor System

FIGS. 1-4 illustrate an exemplary configuration of a flow sensor system 200 of the present disclosure. Referring to FIGS. 1-4, a flow sensor system 200 of the present disclosure includes two main assemblies which fit together prior to use: a flow sensor 210 and a base 220. In one example, the flow sensor 210 can be a single-use flow sensor which is engageable with a reusable base 220. The flow sensor system 200 is an intelligent injection port. The flow sensor system 200 is attachable to an injection site ("Y Site" or stop cock, for example) for manually administered IV injections.

The flow sensor system 200 of the present disclosure can reduce medication error at bedside during bolus delivery. The flow sensor system 200 of the present disclosure can also provide a record of and electronically measure bolus delivery, which allows monitoring bolus delivery and automatic documentation of bolus delivery as part of a patient's health record. The flow sensor system 200 of the present disclosure can also provide alerts when bolus delivery inconsistent with a patient's medical record is about to occur.

Referring to FIGS. 1-4, in one example, the base 220 is a non-sterile, reusable device that houses a battery, a scanner (either optical, mechanical, inductive, capacitive, proximity, or RFID), electronics, and a wireless transmitter. In some examples, the base 220 is battery powered and rechargeable. In some examples, each base 220 has a unique serial number imprinted on a surface of the base 220 or embedded therein that may be transmitted to a data system before use. The data system can be a local computer or tablet "computer", a cellular phone, another medical device, or a Hospital Data System.

Referring to FIGS. 1-4, in one example, the base 220 is removably connectable to the flow sensor 210 and includes at least one deflectable wing tab 280 defining an opening for receiving at least a portion of the flow sensor 210 therein and for securing the flow sensor 210 within a portion of the base 220 prior to use. In one example, a pair of wing tabs 280 secure the flow sensor 210 within the base 220. The wing tabs 280 may be flexible to the extent that they may be outwardly deflected to allow for passage of the flow sensor 210 thereover. In one example, the flow sensor 210 is a pre-sterilized disposable device having an injection port 130 and a distal tubing connection, such as a Luer tip 109, which may be optionally covered by a Luer cap 108.

Figure 3:
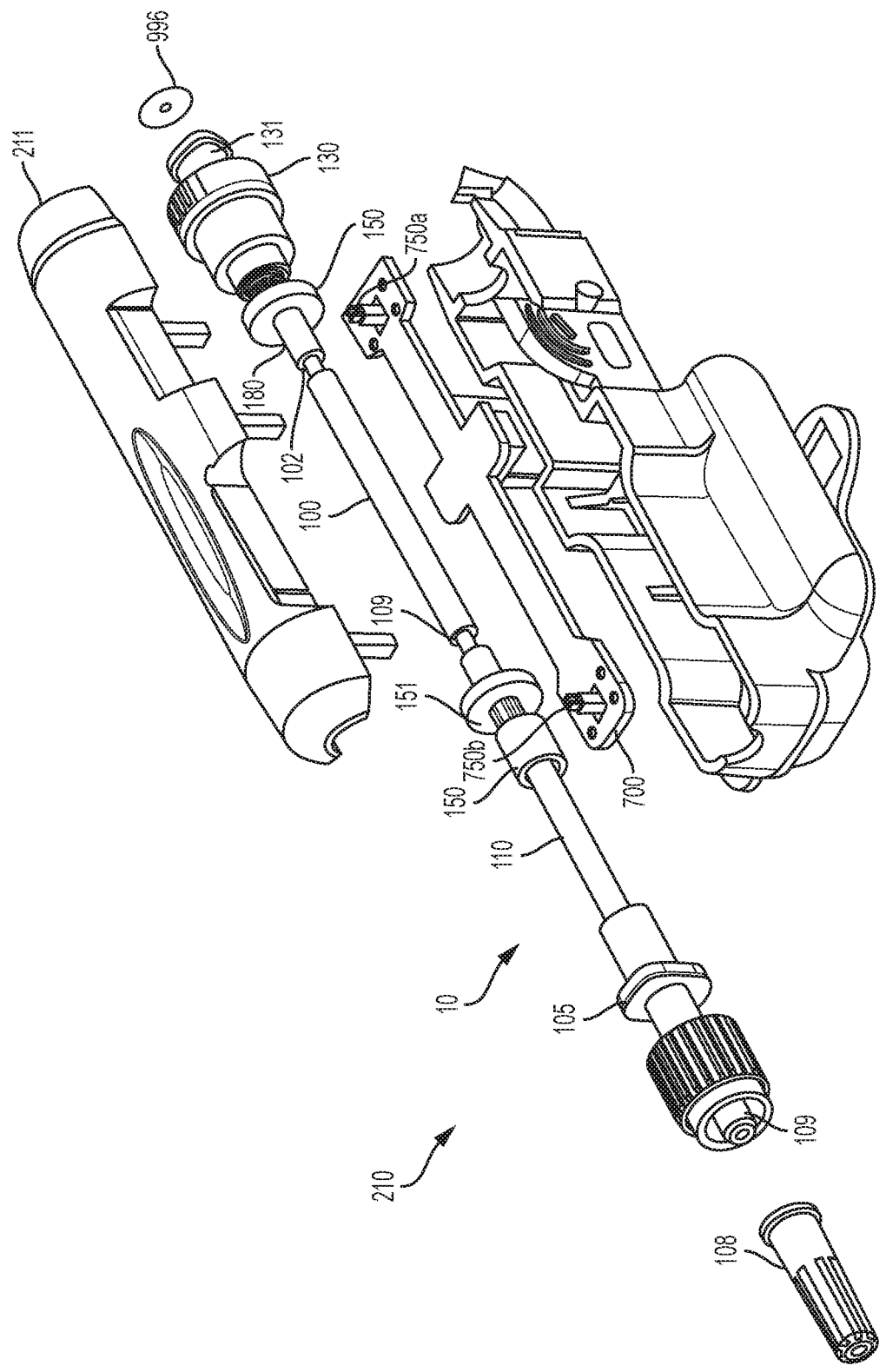
FIG. 3 is an exploded, perspective view of a flow sensor of a flow sensor system in accordance with an example of the present invention.
Figure 4:
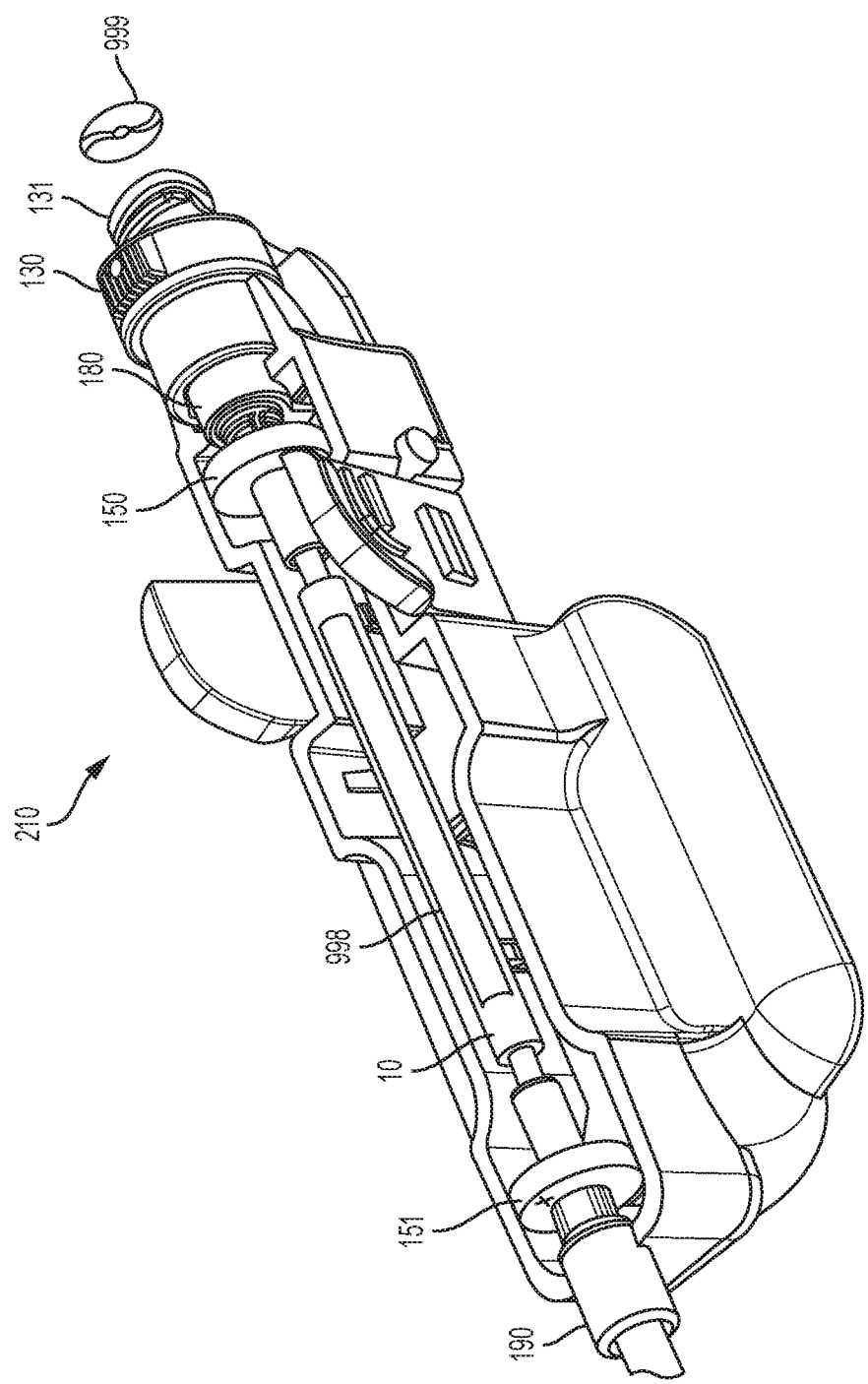
FIG. 4 is a perspective view of a flow sensor of a flow sensor system in accordance with an example of the present invention.

With reference to FIG. 3, the flow sensor 210 may include a flow tube sub-assembly 10 consisting of a flow tube 100 having an outlet end 101 and an inlet end 102. The outlet end 101 may be provided in fluid communication with an outlet tubing 110 having an outlet connection 105 including a Luer tip 109 which may be optionally covered by a flow restrictor, as described herein. In a preferred example, the outlet connection 105 is a plastic connector with a Luer tip 109, however, any suitable method to inject the medicament into a patient is envisaged to be within an aspect of an example of the invention. For example, it may be desirable to replace the outlet connection 105 and tubing 110 with a needle for direct injection/infusion into a patient. In some examples, components of the flow tube sub-assembly 10, such as the flow tube 100 and sensor fittings, can be pre-processed or post-processed using plasma etching, abrasive polishing, and/or reaming to reduce surface roughness of the components of the flow tube sub-assembly 10, which can reduce the formation of micro-bubbles at the inner walls of flow tube 100.

The inlet end 102 may be coupled to the reservoir of a medication pen or infusion reservoir. The inlet end 102 of the flow tube 100 may be provided in fluid communication with an injection port 130, and may optionally include a connection such as a threaded Luer lock 131 which is engageable with a source of a fluid to be injected. A pierceable septum (not shown) may be provided with the injection port 130 for maintaining sterility prior to use. In one example, the flow tube 100 is comprised of a medical grade stainless steel and is approximately 50 mm long with a 1.0 mm inner diameter and a 1.6 mm outer diameter.

In one example, the flow sensor system 200 supports injections using any Luer-lock type syringe or liquid medicament container. Additionally, the flow sensor system 200 is designed to work with encoded syringes that have a special barcode identifier on the Luer collar of the syringe, called "encoding". Preferably, encoded syringes include commercially-available drugs in prefilled syringes with a special barcode that stores information about the medication contained within the syringe. Encoded syringes are readyto-use, passive, and disposable. The encoding syringes store the drug name and concentration contained within the syringe. Additional characteristics such as drug source, container size, drug manufacturer source, drug category color, among others, may also be included. When an encoded syringe is attached to the injection port 130 of the flow sensor 210, this barcode information is read by a scanner in the base 220 and wirelessly transmitted by the flow sensor system 200 to the data system. Preferably, the 2-D barcodes will be added to syringes during the filling process. The flow sensor system 200 also accommodates syringes not having encoding.

The present disclosure provides a flow sensor sub-assembly for sensing flow of a fluidic medicament. The flow sensor 210 also includes a first piezo element or an upstream transducer 150 and a second piezo element or a downstream transducer 151. The first piezo element 150 may be provided with an inlet fitting 180, as shown in FIG. 3, for coupling with the injection port 130. Similarly, the second piezo element 151 may be provided with an outlet fitting 190, for coupling with the outlet tubing 110. The first and second piezo elements 150 and 151 are configured to transmit an ultrasonic signal therebetween indicative of a flow of the fluidic medicament in the flow tube 100. In an example, the first piezo element 150 and the second piezo element 151 are annular in shape and encircle the flow tube 100 at each respective mounting point. In some examples, the flow sensor 210 may comprise a measuring instrument as disclosed in U.S. Pat. No. 7,255,006, which is hereby incorporated by reference in its entirety, to measure a flow of the fluidic medicament in the flow tube 100.

The flow sensor 210 includes a first spring contact 750a and a second spring contact 750b. In one example, the spring contacts 750a, 750b are secured to a base 700 that has a circuit for conducting an electrical signal to and from the spring contacts 750a, 750b to a microprocessor. The first spring contact 750a is in electrical communication with a first piezo element 150 and the second spring contact 750b is in electrical communication with a second piezo element 151. The first spring contact 750a has a first contact force against the first piezo element 150 and the second spring contact 750b has a second contact force against the second piezo element 151. The first contact force may be equivalent to the second contact force. The first and second piezo elements 150, 151 vibrate due to fluid flow through the flow tube 100 of the flow sensor 210. Vibration of the first and second piezo elements 150, 151 creates an ultrasonic signal which can be detected and communicated electronically to the microprocessor. The microprocessor is configured to correlate the ultrasonic signal to a fluid flow rate through the flow tube 100 and provide a fluid flow rate output to the user.

Method of Readying a Flow Sensor

Figure 2:
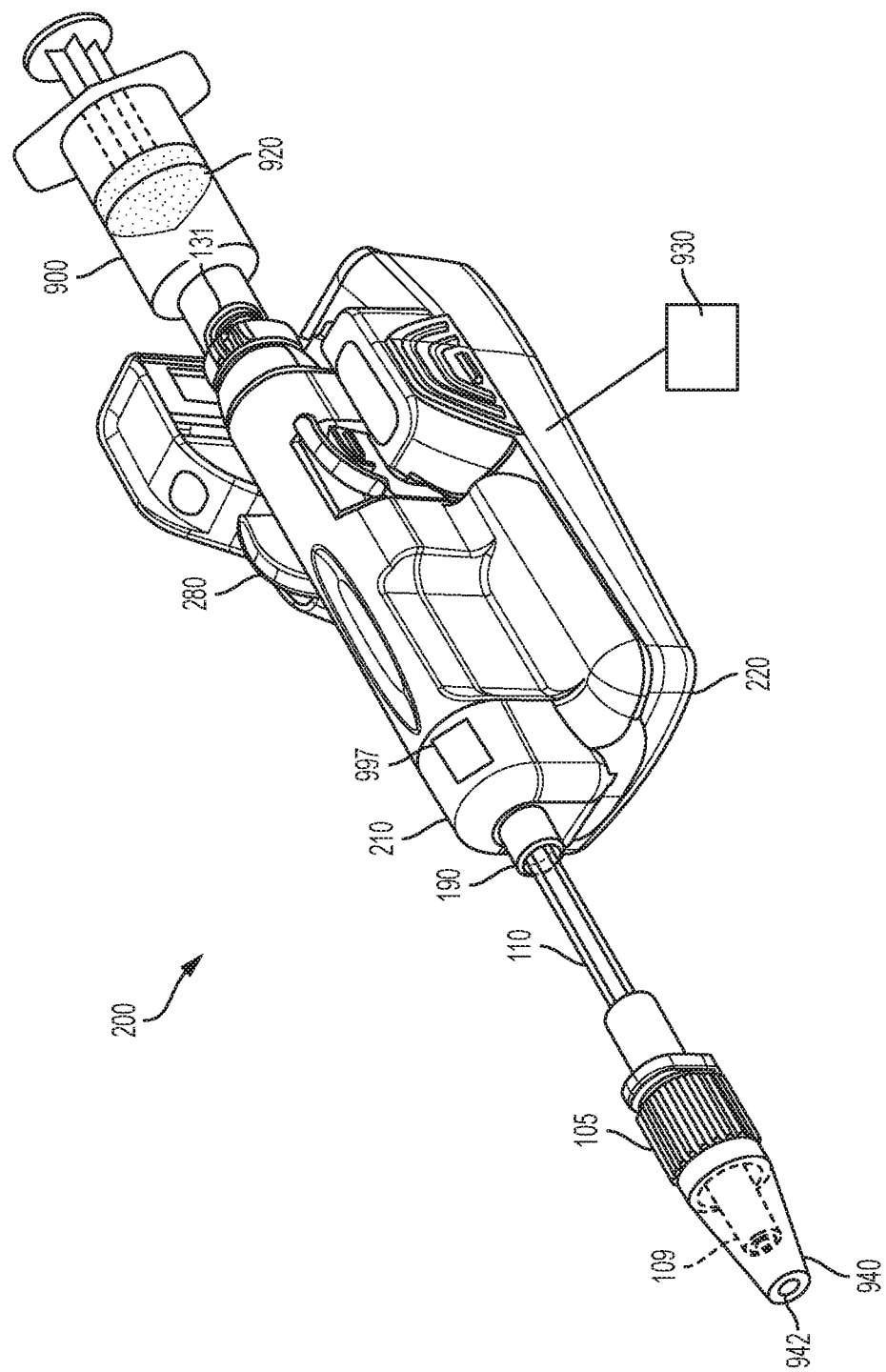
FIG. 2 is a distally-directed perspective view of a flow sensor system in accordance with one example of the present invention.

Referring to FIGS. 1-2, use of a flow sensor system 200 of the present disclosure will now be described. In one example, as the drug is injected, the flow sensor system 200 measures the volume dosed ultrasonically. In order to improve transmission of ultrasonic signals in the flow sensor 210, the present disclosure proposes various examples of increasing a fluid pressure in the flow sensor 210.

During manufacture, flow sensor 210 may be calibrated on a calibration bench. For example, a fluid, such as water, is flowed through the flow sensor 210 to calibrate the ultrasonic signal transmission between the first and second piezo elements 150 and 151. Prior to packaging the flow sensor 210 for shipping, the flow sensor 210 may be dried, such as using hot air, to eliminate any residual fluid that may remain in the flow sensor 210. Without intending to be bound by theory, hot air drying of the fluid path surfaces of the flow sensor 210 contributes to making these fluid path surfaces exhibit their inherently hydrophobic characteristics. In this manner, when the flow sensor 210 is readied for use by priming the flow sensor 210 with a priming fluid, the interior fluid path surface of the flow sensor 210 may not be fully wetted with the priming fluid. Because the flow sensor 210 is configured to generate ultrasonic signals corresponding to a flow rate of the fluid through contact with the internal flow path of the flow sensor 210, the inherently hydrophobic characteristics of the interior surface of the fluid path contribute to a decrease in the ability of the flow sensor 210 to transmit ultrasonic waves. It has been found that wetting the internal surfaces of the flow path through the flow sensor 210, such as by increasing a pressure or maintaining a pressure within the flow path, increases the ultrasonic signal transmission capability of the flow sensor 210.

With reference to FIG. 1, a first method of readying the flow sensor 210 will now be described. In this example, the flow sensor system 200 is prepared for use by attaching the injection port 130 of the flow sensor system 200 to an administrable fluid source, such as a syringe 900 containing a fluid. In some examples, the syringe 900 may contain a priming fluid, such as saline. Prior to connecting the syringe 900, the injection port 130 is desirably cleaned by swabbing the hub according to normal hospital procedure. The syringe 900 can be attached to the injection port 130 by rotating the syringe 900 about its longitudinal axis until the syringe 900 stops, i.e., a secure connection between the syringe 900 and the injection port 130 is made. The syringe 900 has a plunger 920 for delivering the priming fluid from an interior of the syringe 900 when the plunger 920 is pushed in a distal direction.

In some examples, a flow director 999 can be attached between the injection port 130 and the syringe 900. The flow director creates a spiral fluid flow in the fluid delivered from the syringe 900 to the flow path in the fluid sensor 210, which can increase an amount of micro-bubbles dislodged from the inner walls of the flow path of the fluid sensor 210 and/or increase absorption of the micro-bubbles in the fluid.

The outlet connection 105 is capped with a flow restrictor, such as a cap 910. In some examples, the cap 910 is configured to interface with the Luer tip 109 of the outlet connection 105. The cap 910 can be attached to the Luer tip 109 by rotating the cap 910 about its longitudinal axis until the cap 910 stops, i.e., a secure connection between the cap 910 and the Luer tip 109 is made. Once connected to the Luer tip 109, the cap 910 blocks fluid flow from the outlet connection 105.

In some examples, a negative pressure can be applied to the fluid in an administrable fluid source, e.g., the syringe 900, before delivering the fluid from the syringe 900 to the flow path of the flow sensor, thereby degassing the fluid in the syringe 900. For example, a vacuum device 996 as shown in FIG. 3, such as a manual elastomeric suction cup, can be attached to the injection port 130 of the flow sensor 210 before attaching the injection port 130 of the flow sensor system 200 to an administrable fluid source, e.g., before delivering fluid into and/or through the flow sensor 210. The vacuum device 996 can be actuated to apply the negative pressure to the fluid in the syringe 900, which can reduce the partial pressure of syringe 900 before delivering the fluid from the syringe 900 to the fluid sensor 200.

In some examples, one or more surfactants, such as those disclosed in U.S. Pat. Nos. 7,264,885 and 7,560,494, which are hereby incorporated in their entirety by reference, are used to wet the internal surfaces of the flow path of the flow sensor 210 before delivering the fluid into and/or through the flow sensor 210, which can increase contact of the fluid with the internal surfaces of the flow path.

After the syringe 900 is attached to the injection port 130 and the outlet connection 105 is capped with a flow restrictor, the plunger 920 of the syringe 900 is pushed in the distal direction to deliver fluid from the syringe 900. Because the cap 910 prevents fluid from flowing out of the outlet connection 105, the priming fluid from the syringe 900 builds fluid pressure within the flow sensor 210. In some examples, an increased fluid pressure of 5-50 psi within the flow sensor 210 can be maintained for a predetermined period of time. For example, the predetermined period of time may be approximately 1-60 seconds. In other examples, a fluid pressure of greater than 50 psi within the flow sensor 210 can be maintained for a predetermined period of time, which may be greater than 60 seconds.

In some examples, a constant pressure can be applied to the fluid in the flow sensor 210 over a period of time. The constant pressure may be a constant positive pressure or a constant negative pressure. A syringe actuation device, e.g., a bar clamp and spreader, may be attached to the syringe 900 to apply a constant force to the plunger 920 of the syringe 900, which results in the constant pressure being applied to the fluid in the flow sensor 210 capped with the cap 910. For example, the syringe actuation device can be adjusted to a first position in which the syringe actuation device applies the constant force to the plunger of the syringe.

In another example, a bi-directional flow of the fluid can be created in the in the flow path of the flow sensor 210. A first constant pressure can be applied to the fluid in the flow sensor 210 over a first period of time, and a second constant pressure can be applied to the fluid in the flow sensor 210 over a second period of time that is one of before the first period of time and after the first period of time. The first constant pressure may be a positive or negative constant pressure, and the second constant pressure is the other of the positive or negative constant pressure. A syringe actuation device, e.g., a bar clamp and spreader, may be attached to the syringe 900 and adjusted to a first position in which the syringe actuation device applies a first constant force to the plunger 920 of the syringe 900, thereby applying the first constant pressure to the fluid in the flow sensor 210 over the first period of time. The syringe actuation device 944 can be adjusted to a second position in which the syringe actuation device 944 a second constant force to the plunger 920 of the syringe 900, thereby applying the second constant pressure to the fluid in the flow sensor 210 over the second period of time. For example, the syringe actuation device may be adjusted to a position that depresses the plunger 920 of the syringe 900 to deliver the fluid into and/or through the flow sensor 210 and apply a positive pressure thereto. The syringe actuation device can maintain the syringe in the depressed position for a desired or predetermined period of time. The syringe actuation device may be adjusted after the first period of time to a position that pulls the plunger 920 of the syringe in an opposite direction of the direction that depresses the plunger to apply a negative pressure to the fluid in the flow sensor 210, thereby creating a flow of the fluid from the outlet connection 105 toward the injection port 130. The syringe actuation device can maintain the syringe in the pulled-back position for a desired or predetermined period of time. The syringe actuation device can be alternated between the positions to create a chaotic bi-directional flow of the fluid in the flow sensor 210.

In some examples, a pressure sensor can be connected between the syringe 900 and the injection port 130. The pressure sensor can be configured to measure a pressure in the fluid flow sensor 210 and provide an output of the measured pressure to a user. The user can adjust the syringe actuation device based on the measured pressure to achieve a desired pressure in the flow sensor 210. In another example, the pressure sensor can communicate with the controller 930 or another computing device configured to automatically control an electromechanical syringe actuation device based on the measured pressure to achieve the desired pressure in the flow sensor 210.

As discussed herein, the syringe actuation device may comprise a clamp, such as a bar clamp and spreader, that can be adjusted between positions that maintain the plunger 920 in various depressed and/or pulled-back positions. In another example, the syringe actuation device may comprise a piston or rod configured to engage the plunger 920 of the syringe 900 in a manner that enables the piston to depress the plunger 920 distally when advanced and pull-back the plunger 920 proximally when retracted. The piston or rod may be driven by a rotational mechanism, such as included in the force limiting device 1010 described herein with respect to FIG. 8, a latching mechanism, such as included in a spring biased grip drive or a ratchet driven grip drive, e.g., as used in well-known caulking guns, and/or as described herein with respect to the force limiting device 1030 described with respect to FIG. 9, or a linear force mechanism that applies a direct linear force to the piston, such as a loaded spring or a ratcheting mechanism as described herein with respect to the force limiting device 1050 described with respect to FIG. 10. In other words, the force limiting devices 1010, 1030, and 1050 described herein with respect to FIGS. 8, 9, and 10, respectively, each include a syringe actuation device according to non-limiting embodiments or aspects of the present invention.

Regardless of a type of syringe actuation device used to apply a force to the plunger, it is contemplated that the syringe actuation device can be configured to be manually driven and controlled or configured to be automatically driven and controlled by a computing device, such as the controller 930, based on input from at least one sensor, such as the pressure sensor, a flow rate sensor, a volume sensor, a timer, or any combination thereof. For example, the controller 930 or another computing device may compare a current pressure of the fluid in the fluid sensor determined by the pressure sensor to a desired pressure and control an operation of the syringe actuation device to adjust the plunger to achieve the desired pressured based on the current pressure.

Figure 7:
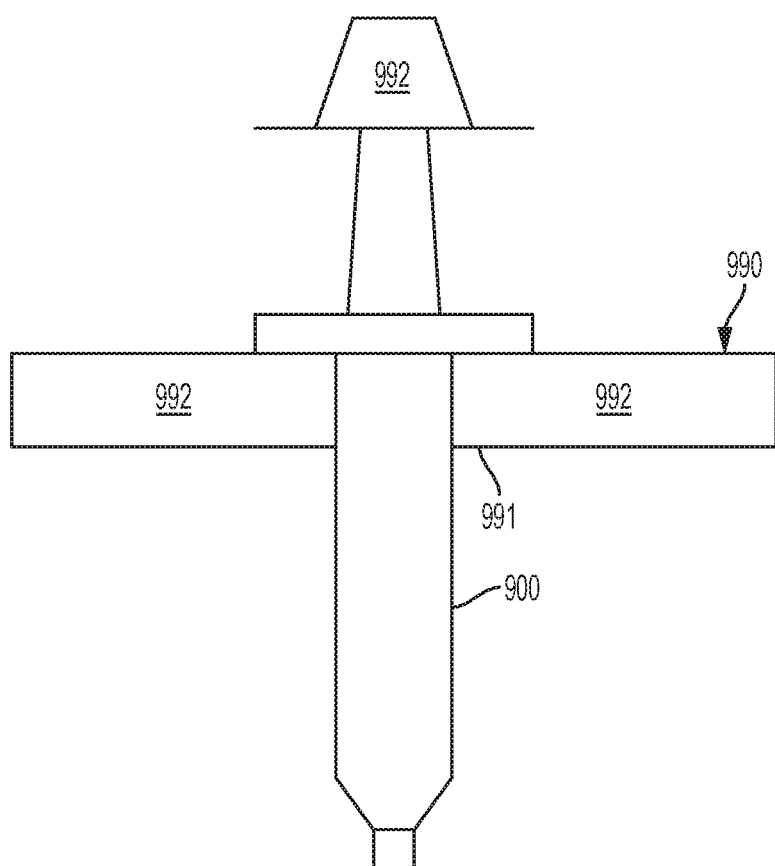
FIG. 7 illustrates a holder for a syringe in a flow sensor system in accordance with an example of the present invention.

In another example, with respect to FIG. 7, the syringe 900 can be mounted vertically in a syringe holder 990. The syringe holder 990 may comprise an opening 991 configured to receive the syringe 900. Flanges of the syringe 900 may on laterally extending surfaces 992 of the syringe holder 990. The distal end of the syringe 900 extends through the opening 991 and is accessible for connection to the injection port 130 of the fluid sensor 210. A load 992 can be applied to the plunger 920 of the syringe 900 while the syringe 900 is held in the vertical orientation by the syringe holder 990. The load 992 applies a constant force or pressure to the plunger 920, thereby resulting in a constant pressure being applied to the fluid in the flow sensor 210 over a period of time that the load is applied.

While the flow sensor 210 is pressurized by the fluid from the syringe 900, at least one first signal is generated by the flow sensor 210 to characterize at least one attribute of fluid. In various examples, the at least one attribute may be fluid flow rate and/or fluid pressure. The manual increase of fluid pressure within the flow sensor 210, while keeping the outlet connection 105 capped, helps eliminate any air between the interior surface of the flow path of the flow sensor 210 and the fluid. In this manner, the interior surface of the flow path of the flow sensor 210 is fully wetted to allow for an increased ultrasonic signal transmission of the flow sensor 210.

Next, the pressure on the plunger 920 of the syringe 900 can be released, and the cap 910 is removed from the Luer tip 109. The outlet connection 105 is attached to an inlet of a fluid pathway (not shown) configured for delivering fluid from an administrable fluid source, such as the syringe 900, to a patient. In some examples, the fluid pathway may be a catheter configured for connecting to a patient. Prior to connecting the fluid pathway to the patient, fluid from the syringe 900 is first expelled from the fluid pathway, such as during the priming of the fluid pathway. As the fluid is delivered from the syringe 900, the fluid flows through the flow sensor 210 and out of the fluid pathway. In some examples, 2-7 ml of fluid may be delivered from the syringe 900 through the fluid pathway. The flow sensor 210 may generate at least one second signal of the same type as the first signal in order to characterize at least one attribute of the fluid. For example, the second signal may characterize the pressure and/or flow rate of fluid through the flow sensor 210. In some examples, the second signal may be increased (i.e., have higher strength) than the first signal due to the internal surfaces of the flow path of the flow sensor 210 being fully wetted. For example, the second signal may be increased over the first signal by 120%, 160%, or 180%, inclusive of the values therebetween. The flow sensor 210 is now primed and ready for use in a fluid delivery procedure.

In some examples, the flow sensor 210 can be shook or vibrated when the fluid is within the fluid channel, thereby dislodging micro-bubbles from the inner walls of the flow sensor 210. The dislodged micro-bubbles can be removed from the flow sensor 210 by flushing the fluid from the flow sensor 210. In one example, the flow sensor 210 can be manually shook or vibrated. In another example, as shown in FIG. 2, a vibrator 997 can be attached to the flow sensor 210 or directly to the flow tube sub assembly 10 to shake or vibrate the flow sensor 210. In another example, the first piezo element or the upstream transducer 150 and/or the second piezo element or the downstream transducer 151 can be activated to apply an ultrasonic transmission to the flow sensor 210 to dislodge micro-bubbles from the inner walls of the flow path of the flow sensor 210. The first and second piezo elements 150, 151 can be activated before or without taking a measurement therewith. As the fluid is delivered from the syringe 900 after vibrating the flow sensor 210 or activating the first and second piezo elements 150, 151, the fluid flows through the flow sensor 210 and out of the fluid pathway, carrying dislodged micro-bubbles out of the flow sensor 210.

In another example, the fluid within the flow sensor 210 can be heated, which can expand a gas carrying capacity of the fluid prior to flushing the fluid out of the flow sensor 210. For example, a heating element 998, such as a variable resistor heating element, can be attached to the flow tube sub assembly 10 or another element of the flow sensor 210 and apply heat to the flow tube sub assembly 10 including the fluid in the fluid sensor 210 before the fluid is flushed from the fluid sensor 210. By increasing the gas carrying capacity of the fluid, more micro-bubbles can be carried by the fluid out of the flow sensor 210 when the fluid is flushed from the flow sensor 210.

In various examples, the flow sensor 210 may be in communication with a controller 930. The controller 930 may be configured for receiving information from the flow sensor 210, such as receiving the at least one first signal and the at least one second signal. The controller 930 may be configured to determine that the at least one attribute of the fluid based on the received data from the at least one first signal and the at least one second signal matches at least one condition specified by at least one rule. For example, the controller 930 may be configured for identifying a type of fluid flowing through the flow sensor 210 based on a flow rate of the fluid through the flow sensor 210 for a given fluid pressure at a given fluid temperature. Without intended to be bound by theory, each fluid, such as a fluid medicament, has a unique ultrasonic signature as the fluid flows through the flow sensor 210. The ultrasonic signature may be a function of fluid pressure, temperature, and material composition of the fluid.

In various examples, the controller 930 may generate at least one operation modification signal in response to the characterized at least one attribute matching at least one condition specified by at least one rule. For example, the controller 930 can execute a flow algorithm based on data representing characteristics or attributes of the fluid flow received from the piezo elements 150, 151. In some examples, the syringe 900 may have indicia that, when read by a reading device of the flow sensor system 200 that is in operative communication with the controller 930, causes the controller 930 to initiate a predetermined operating cycle. In some examples, the indicia may be a 2D or 3D barcode, QR code, or any other indicia capable of storing information that, when read by a reading device of the flow sensor system 200, is configured to be interpreted as a set of instructions to be performed by the controller 930. For example, the indicia, when read by the reading device, can cause the controller 930 to initiate a priming cycle for priming the flow sensor 210. In some examples, the priming cycle may comprise generating at least one signal, such as a first signal and a second signal discussed herein.

The controller 930 may transmit, by a transmitter (not shown) the operation modification signal to at least one device. In some embodiments, if a fluid type is determined to be a different type than a desired fluid type, or if a flow rate is determined to be a different flow rate than a desired flow rate, the controller 930 can transmit an operation modification signal to a display and/or a data processing module that causes the module to display an alarm or alert or causes the module to transmit a signal back to the system 200 that stops the fluid flow. The controller 930 can further control the wireless transmitter to transmit injection data representing a type of medication, a dose of a medication, and/or a time of a dose of a medication to the display and/or data processing module. In some embodiments, the controller 930 can automatically transmit the data to the module in response to an automated injection.

Figure 5:
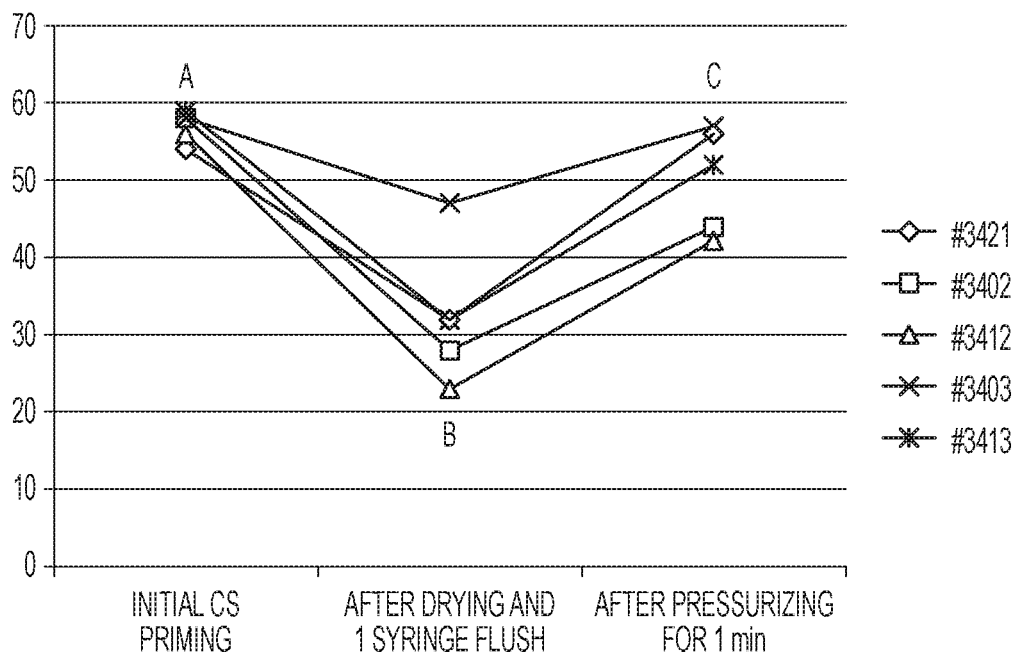
FIG. 5 is a graph showing signal level of a flow sensor of a flow sensor system as a function of time according to one example case.

With reference to FIG. 5, a graph depicting a percentage of signal strength of five flow sensors 210 as a function of time is shown in accordance with one example. Each flow sensor 210 was initially calibrated using a standard calibration routine. The signal readings from each of the flow sensors 210 after calibration are shown as point A on the graph. The flow sensors 210 were then dried with hot air and flushed with a priming fluid without being pressurized. Ultrasonic signal transmission readings were then recorded, shown as point B on the graph. From the graph in FIG. 5, it can be readily observed that signal strength drops for each of the flow sensors 210 after the flow sensors 210 have been dried with hot air. In order to increase the signal level, each flow sensor 210 was capped with a cap 910 and pressurized with a priming fluid, such as saline, for 60 seconds. After the expiration of the pressurization period, another signal reading was taken. Point C in FIG. 5 illustrates that the signal level increases from Point B after the flow sensors 210 have been pressurized with a priming fluid.

With reference to FIG. 2, instead of capping the outlet connection 105 with a cap 910, such as described herein with reference to FIG. 1, the outlet connection 105 may be connected to a vented flow restrictor, such as a vented cap 940. The vented cap 940 comprises an orifice or outlet 942 that provides a fluid flow path from the outlet connection 105 through the vented cap 940 to atmosphere. In some examples, the vented cap 940 may be a needle having an inner diameter sufficiently small to be capable of generating back pressure in the flow sensor 210 when fluid is delivered from the syringe 900. For example, the vented cap 940 may be a needle having an outlet of approximately 30 G (0.16 mm inner diameter (ID)). In other examples, the vented cap 940 may have an inner diameter of 0.1-0.2 mm. In another example, the vented cap 940 may comprise a smaller orifice or outlet 942, for example an outlet of less than 30 G (0.16 mm ID), for example, an outlet of approximately 34 G (0.0826 mm ID) or less. The priming fluid delivered from the syringe 900 builds back pressure within the flow sensor 210. In some examples, an increased fluid pressure of 5-50 psi or greater within the flow sensor 210 can be maintained for a predetermined period of time. For example, the predetermined period of time may be approximately 1-60 seconds.

In another example, a varying pressure can be applied to the fluid in the flow sensor 210. The vented cap 940 can be configured to change an inner diameter of the orifice or outlet 942 of the vented cap 940 as a function of the fluid pressure within the fluid sensor 210. For example, the vented cap 940 can comprise an elastomeric material having an elasticity that enables the outlet 942 to deform in response to applied pressure. When a pressure within the flow sensor 210 is sufficient to overcome the elasticity of the outlet 942 of the vented cap 940, for example, in response to a build-up of pressure within the flow sensor 210 from the delivery of the priming fluid, the outlet 942 of the vented cap 940 deforms in response to the increased pressure to increase the inner diameter. The increase in the inner diameter of the outlet 942 of the vented cap 940 enables a higher rate of fluid flow from the vented cap 940, which can reduce the back pressure in the flow sensor 210. When the back pressure in the fluid sensor 210 is no longer sufficient to overcome the elasticity of the outlet 942 of the vented cap 940, the inner diameter of the outlet 942 of the vented cap 940 returns to its original or resting diameter. If the priming fluid is continued to be delivered, the back pressure in the flow sensor 210 may begin increasing again until the pressure is again sufficient to overcome the elasticity of the outlet 942. The inner diameter of the outlet 942 of the vented cap 940 can thus be changed over time to create a perturbative fluid flow within the fluid sensor 210 during priming, which can improve wetting of the interior surface of the flow path of the flow sensor 210 to allow for an increased ultrasonic signal transmission of the flow sensor 210.

In some examples, a flow rate of the fluid delivered from the administrable fluid source to the fluid channel through the fluid inlet can be varied. For example, the delivering the fluid from the syringe 900 to the fluid sensor 210 may comprise delivering boluses of the fluid to the flow path of the fluid sensor 210. The boluses may be periodically delivered to the fluid channel at standard or variable time intervals. The boluses may be varied from one another by at least one of: a volume of the boluses, a pressure applied to the fluid of the boluses within the flow sensor 210, a period of time over which the pressure is applied to the fluid of the boluses within the flow sensor 210, or any combination thereof. In one implementation, an electromechanical device can be configured to automatically deliver the boluses to the fluid sensor at the periodic time intervals.

Figure 8:
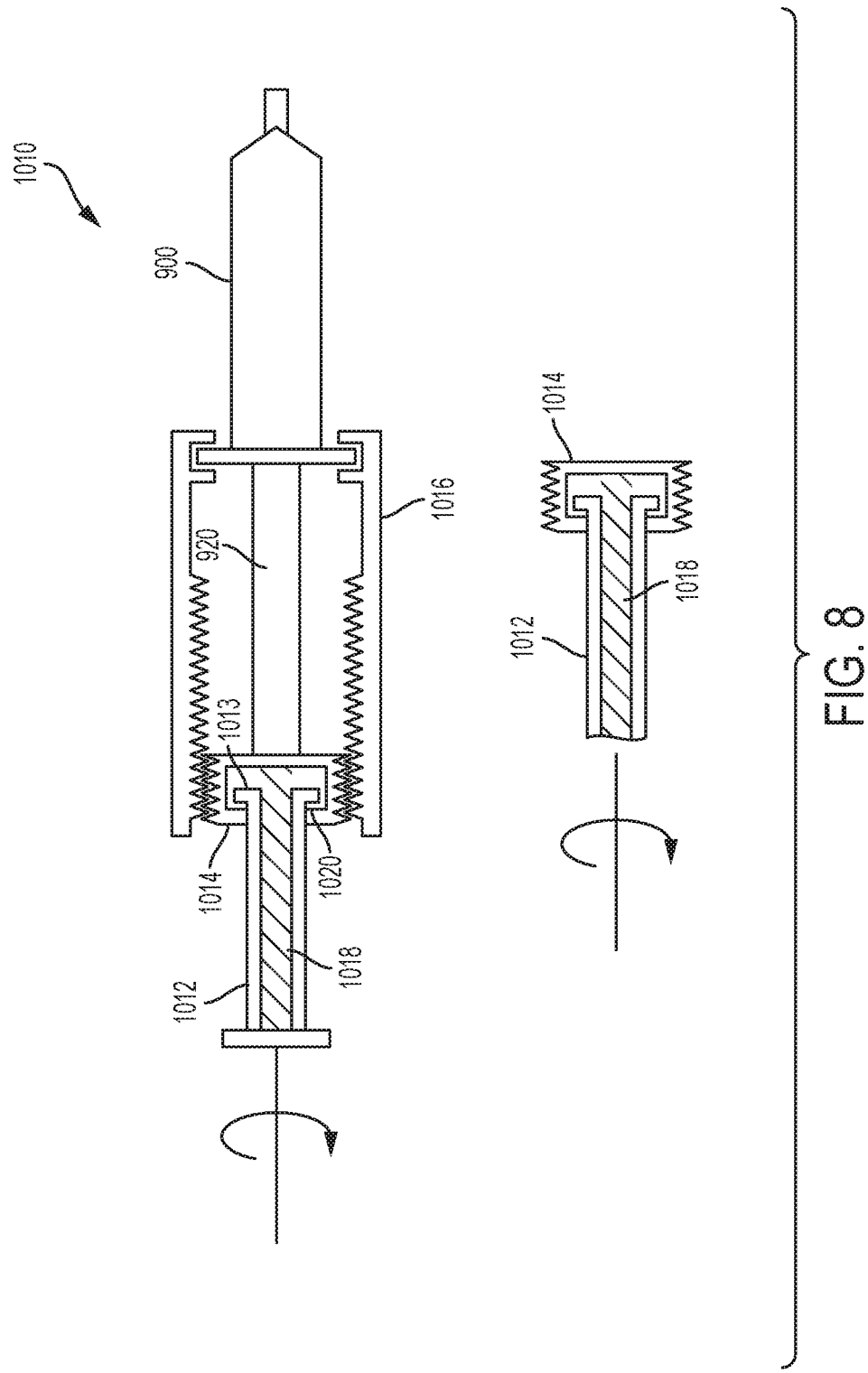
FIG. 8 illustrates an exemplary configuration of a force limiting device of a flow sensor system in accordance with an example of the present invention.
Figure 9:
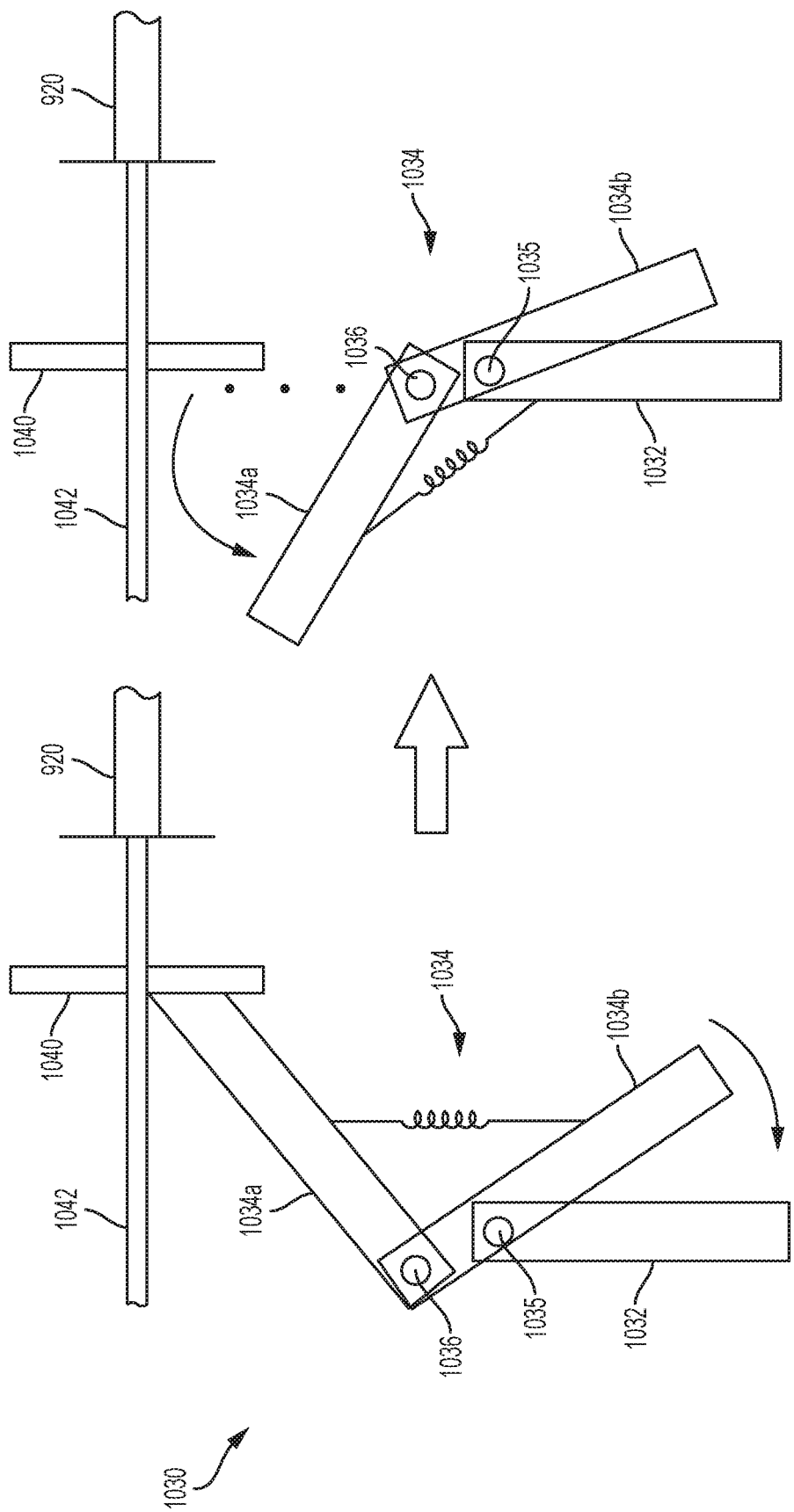
FIG. 9 illustrates an exemplary configuration of a force limiting device of a flow sensor system in accordance with an example of the present invention.
Figure 10:
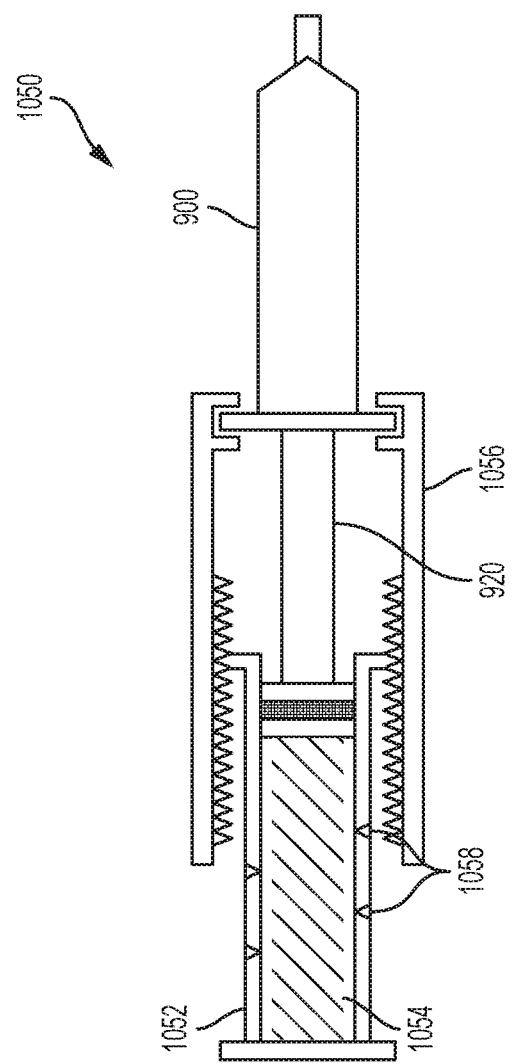
FIG. 10 illustrates an exemplary configuration of a force limiting device of a flow sensor system in accordance with an example of the present invention.

In some examples, a force limiting device 1010, 1030, or 1050, such as described herein with respect to FIGS. 8, 9, and 10, respectively, can be attached to the syringe 900. The force limiting device 1010, 1030, or 1050 may include a syringe actuation device as described. The force limiting device 1010 or 1030 may inhibit an application of a pressure to the fluid in the fluid channel of the fluid sensor 210 that violates a threshold pressure. For example, the force limiting device 1010 or 1030 may inhibit movement of the plunger 920 of the syringe 900 (or a syringe actuation device thereof driving the plunger 920) in response to the application of the pressure to the fluid in the fluid channel of the fluid sensor 210 that violates the threshold pressure. In another example, the force limiting device 1050 may include at least one pressure indicator that indicates a current pressure applied to the fluid in the fluid channel.

While the flow sensor 210 is pressurized by the fluid from the syringe 900, at least one first signal is generated by the flow sensor 210 to characterize at least one attribute of fluid. In various examples, the at least one attribute may be fluid flow rate and/or fluid pressure. The manual increase of fluid pressure within the flow sensor 210, while keeping the outlet connection 105 capped, helps eliminate any air between the interior surface of the flow path of the flow sensor 210 and the fluid. In this manner, the interior surface of the flow path of the flow sensor 210 is fully wetted to allow for an increased ultrasonic signal transmission of the flow sensor 210.

Next, the pressure on the plunger 920 of the syringe 900 can be released, and the vented cap 940 is removed from the Luer tip 109. The outlet connection 105 is attached to an inlet of a fluid pathway (not shown) configured for delivering fluid from an administrable fluid source, such as the syringe 900, to a patient. In some examples, the fluid pathway may be a catheter configured for connecting to a patient. Prior to connecting the fluid pathway to the patient, fluid from the syringe 900 is first expelled from the fluid pathway, such as during the priming of the fluid pathway. As the fluid is delivered from the syringe 900, the fluid flows through the flow sensor 210 and out of the fluid pathway. In some examples, 2-7 ml of fluid may be delivered from the syringe 900 through the fluid pathway. The flow sensor 210 may generate at least one second signal of the same type as the first signal in order to characterize at least one attribute of the fluid. For example, the second signal may characterize the pressure and/or flow rate of fluid through the flow sensor 210. In some examples, the second signal may be increased (i.e., have higher strength) than the first signal due to the internal surfaces of the flow path of the flow sensor 210 being fully wetted. For example, the second signal may be increased over the first signal by 120%, 160%, or 180%, inclusive of the values therebetween. The flow sensor 210 is now primed and ready for use in a fluid delivery procedure.

Figure 6:
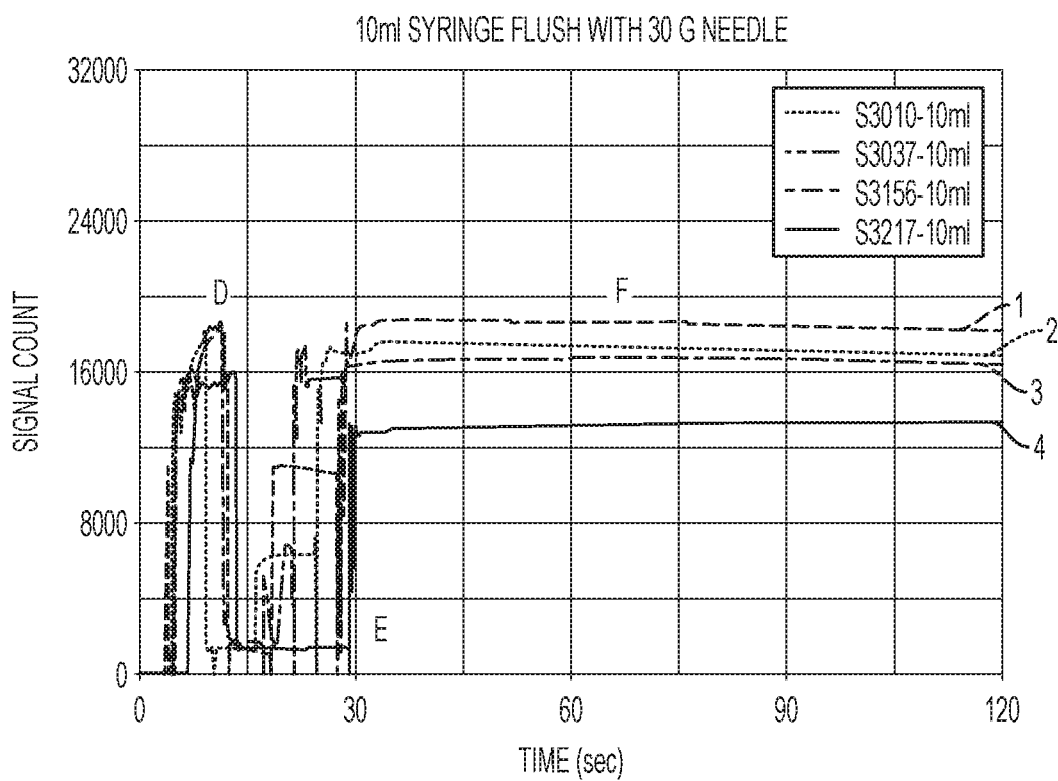
FIG. 6 is a graph showing signal level of a flow sensor of a flow sensor system as a function of time according to another example case.

With reference to FIG. 6, a graph depicting signal level of three flow sensors 210 (labeled 1, 2, 3) as a function of time is shown in accordance with another example. Each flow sensor 210 was provided with a vented cap 940 having a 30 G needle. A signal count was recorded (Point D) during a delivery of 2 ml of fluid from the syringe 900. The vented cap 940 was then removed from each flow sensor 210 and a signal count illustrative of a pressure drop was recorded (Point E). From the graph in FIG. 6, it can be readily observed that signal strength drops for each of the flow sensors 210 after the vented cap 940 is removed from the flow sensors 210. After removing the vented cap 940, 7 ml of fluid was delivered from the syringe 900 through each flow sensor 210. During this step, signal count increased and stabilized at a high value (Point F). A signal level of a fourth flow sensor 210 (labeled 4 in FIG. 6), which has been primed without using the vented cap 940, is shown as a comparative example. The signal strength of the fourth flow sensor 210 is significantly lower than a signal strength of flow sensors 210 that were readied using the vented cap 940 in a manner described herein with reference to FIG. 2.

Force Limiting Device for Readying a Flow Sensor

FIGS. 8-10 illustrate exemplary configurations of a force limiting device of a flow sensor system of the present disclosure. Referring to FIG. 8, a force limiting device 1010 for controlling the plunger 920 of the syringe 900 to deliver a fluid from an interior of the syringe 900 comprises an actuator rod 1012 extending from a proximal end to a distal end. A plunger engagement portion 1014 is engaged with the distal end of the actuator rod 1012 and configured to engage the plunger 920 of the syringe 900. For example, an outer wall at the distal end of the plunger engagement portion 1014 can engage the plunger 920. A clutch 1020 engages the distal end of the actuator rod 1012 to the plunger engagement portion 1014. A spring 1018 extends within the actuator rod 1012.

The force limiting device 1010 further comprises a body 1016 having a proximal end, a distal end, and an opening at the proximal end. The opening receives the plunger engagement portion 1014. The plunger engagement portion 1014 is threadably engaged with the body 1016. For example, an inner wall of the body 1016 can comprise male threading or female threading, and an outer wall of the plunger engagement portion 1014 can comprise the other of the male threading or the female threading. In one example, the threading is multi-start high lead thread. The distal end of the body 1016 is configured to connect to the syringe 900, e.g., to a flange on the body of the syringe, and the plunger 920 of the syringe 900 extends within the body 1016 when the syringe 900 is connected to the body 1016. The body 1016, when connected to the syringe 900, prevents axial movement of a body the syringe 900 with respect to the body 1016, while allowing for axial movement of the plunger 920 within the body 1016. In some examples, the body 1016 may be formed of a first half and a second half that can be placed together around the syringe and connected via a snap-fit connection to connect the body 1016 to the syringe 900.

The spring 1018 extends within the actuator rod 1012 and into the plunger engagement portion 1014 via an opening in a proximal end of the plunger engagement portion 1014. The spring 1018 engages an inner wall at the distal end of the plunger engagement portion 1014. The actuator rod 1012 extends into the plunger engagement portion 1014. A portion of the actuator rod 1012 that extends within the plunger engagement portion 1014 includes a radially extending flange 1013. The clutch 1020 connects a proximal face of the radially extending flange 1013 to the inner wall at the proximal end of the plunger engagement portion 1014.

The clutch 1020 is configured to disengage the distal end of the actuator rod 1012 from the plunger engagement section 1014 in response to a compression of the spring 1018. For example, a spring constant of the spring 1018 may determine a force required to disengage the clutch 1020. The spring 1018 compresses in response to a plunger reaction force applied by the plunger 920 of the syringe to the plunger engagement portion 1014. The compression of the spring 1018 enables the actuator rod 1012 to move distally with respect to the plunger engagement portion 1014, such that the proximal face of the radially extending flange 1013 disengages and separates in the distal direction from the inner wall at the proximal end of the plunger engagement portion 1014, thereby disengaging the clutch 1020. For example, the plunger reaction force applied to the plunger engagement portion 1014 by the plunger 920 is transferred to the spring 1018, which compresses the spring 1018.

The plunger engagement portion 1014 is configured to inhibit an application of a force to the plunger 920 of the syringe 900 that violates a threshold force. For example, the plunger engagement 1014 can portion inhibit movement of the plunger 920 of the syringe 900 in response to a plunger reaction force applied by the plunger 920 of the syringe to an outer wall at the distal end of the plunger engagement portion 1014. With the clutch 1020 engaged, a rotational force applied to the actuator rod 1012 is transferred to the plunger engagement portion 1014, which rotates in the threaded engagement with the body 1016 to move the plunger engagement portion 1014 axially with respect to the body 1016. With the clutch 1020 disengaged, a rotational force applied to the actuator rod 1012 is not transferred to the plunger engagement portion 1014, thereby inhibiting further axial movement of the plunger engagement portion 1014 with respect to the body 1016 and an application of a force to the plunger 920 of the syringe 900 that violates a threshold force set by the spring 1018.

Referring to FIG. 9, a force limiting device 1030 for controlling the plunger 920 of the syringe 900 to deliver a fluid from an interior of the syringe 900 comprises a handle 1032 and a cooperating trigger 1034, which may be connected by a first joint 1035. The trigger 1034 comprises a first portion 1034a connected to a second portion 1034b by a second joint 1036. A spring 1038 further connects the first portion 1034a to the second portion 1034b.

The handle 1032 and the cooperating trigger 1034 can be configured to operate a latching mechanism, such as included in a spring biased grip drive or a ratchet driven grip drive, e.g., as used in well-known caulking guns. The first portion 1034a of the trigger 1034 is configured to transfer a driving force to the plunger 920 of the syringe 900. The first portion 1034a may be configured to directly engage the plunger 920, or engage the plunger 920 via at least one of a drive grip or plate 1040 and piston 1042, the details and operation of which are well-known to those of skill in the art and, thus, omitted in the interest of brevity. Although not shown in the interest of clarity in the drawings, the force limiting device 1030 may comprise a body extending from the handle 1032 configured to hold the syringe 900 stationary with respect the handle 1032 during operation of the plunger 920 by the force limiting device 1030. Such configurations for holding a fluid container during fluid delivery are well-known to those of skill in the art, examples of which can be found in U.S. Pat. Nos. 4,299,336 and 6,155,463, hereby incorporated by reference in their entirety.

Movement of the trigger 1034 toward the handle 1032 may apply a stretching force to the spring 1038. For example, as the first portion 1034a engages and applies the driving force to the drive plate 1040, a plunger reaction force is applied by the plunger 920 to the first portion 1034a of the trigger 1034 in a direction opposite to the driving force, which may partially or completely inhibit movement of the first portion 1034a with the second portion 1034a, thereby transferring the movement of the second portion 1034b to the spring 1018 as the stretching force. The first portion 1034a of the trigger 1034 disengages the plunger 920 or drive plate 1040 in response to a stretching force greater than a threshold force applied to the spring 1038. For example, a spring constant of the spring 1038 may determine a force required to disengage the first portion 1034a from the plunger 920 or drive plate 1040 such that the first portion 1034a cannot provide the driving force in the direction opposite the plunger reaction force.

In response to a plunger reaction force applied by the plunger 920 the first portion 1034a that is greater than the threshold force, the stretching force applied to the spring 1038 due to the movement of the trigger 1034 toward the handle 1032 exceeds the spring constant of the spring 1018, thereby stretching the spring and increasing a distance between the first portion 1034a and the second portion 1034b until the first portion 1038 is forced to disengage from the plunger 920 or the drive plate 1040. For example, the first portion 1034a may breakaway and invert its position with respect to the joint 1036 as shown in FIG. 9, thereby preventing any further application of force to the plunger 920 via the force limiting device 1030.

Referring to FIG. 8, a force limiting device 1050 for controlling the plunger 920 of the syringe 900 to deliver a fluid from an interior of the syringe 900 comprises an actuator rod 1052 extending from a proximal end to a distal end. A spring 1054 extends within the actuator rod 1052. A distal end of the spring 1054 is configured to engage the plunger 920 of the syringe 900.

The force limiting device 1050 further comprises a body 1056 having a proximal end, a distal end, and an opening at the proximal end, wherein the opening receives the distal end of the actuator rod 1052, and wherein the actuator rod 1052 comprises at least one indicator 1058 that indicates a desired amount of compression of the spring 1054. The distal end of the body 1056 is configured to connect to the syringe, the plunger 920 of the syringe 900 can extend within the body 1056.

In some examples, an outer wall of the actuator rod 1052 may be in ratcheting engagement with an inner wall of the body 1056. For example, a distal end of the actuator rod 1052 may include a radially extending pawl, and the inner wall of the body 1056 may include a plurality of teeth.

At least a portion of the actuator rod 1052 and at least a portion of the body 1056 may be transparent such that the spring 1054 and the plunger 920 are visible through the actuator rod 1052 and the body 1056. A location of the at least one indicator 1058 with respect to a location of at least one of a distal end of the spring 1058 and a proximal end of the plunger 920 can indicate the desired amount of compression of the spring 1058, for example, for during a priming operation as described herein.

In some examples, the actuator rod 1052 may include at least two indicators spaced apart from one another. A location of the at least one of the distal end of the spring 1058 and the proximal end of the plunger 920 between the at least two indicators can indicate the desired amount of compression of the spring 1058.

Method of Using the Flow Sensor System

To use a primed flow sensor system 200, a user attaches the flow sensor 210 to the base 220 by joining the flow sensor 210 (tubing side) and base 220 front sections first, and then snapping the two together. Preferably, an audible snapping sound is heard to indicate a secure connection between the flow sensor 210 and the base 220. In one example, connecting the flow sensor 210 to the base 220 automatically powers on the flow sensor system 200. In one example, the connection of the flow sensor 210 to the base 220 is verified by a blinking light on the base 220. In other examples, other indicators may be used.

The flow sensor system 200 is now ready for delivery of IV medications. In one example, in the event of a flow sensor system 200 failure (excluding the IV fluid pathway), the flow sensor system 200 will still allow standard medication or fluid delivery through the port.

Next, giving an injection using the flow sensor system 200 will be discussed. First, the injection port 130 is cleaned by swabbing the hub according to normal hospital procedure. Next, a syringe 900 can be attached to the injection port 130 of the flow sensor 210 by completely rotating the syringe 900 until the syringe 900 stops, i.e., a secure connection between the syringe 800 and the injection port 130 is made. Ideally, the caregiver double checks each medication name and concentration on the syringe 900 prior to attachment to the injection port 130 to assure the correct medication is given.

The flow sensor 210 can be disposed after the flow sensor 210 is used to sense the flow of at least one fluidic medicament. The flow sensor base 220 can be used with a plurality of different flow sensors 210.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as they become within known or customary practice in the art to which this disclosure pertains and which fall within the limits of the appended claims.

What is claimed is:

1. An apparatus for controlling a plunger of a syringe to deliver a fluid from an interior of the syringe, comprising:
   an actuator rod extending from a proximal end to a distal end;
   a plunger engagement portion engaged with the distal end of the actuator rod and configured to engage the plunger of the syringe; and
   a body having a proximal end, a distal end, and an opening at the proximal end, wherein the opening receives the plunger engagement portion, and wherein the plunger engagement portion is threadably engaged with the body.

2. The apparatus of claim 1, wherein the plunger engagement portion is configured to inhibit an application of a force to the plunger of the syringe that violates a threshold force.

3. The apparatus of claim 1, wherein the plunger engagement portion inhibits movement of the plunger of the syringe in response to a plunger reaction force applied by the plunger of the syringe.

4. The apparatus of claim 1, further comprising a clutch that engages the distal end of the actuator rod to the plunger engagement portion.

5. The apparatus of claim 4, further comprising a spring that extends within the actuator rod.

6. The apparatus of claim 5, wherein the spring extends within the actuator rod and into the plunger engagement portion via an opening in a proximal end of the plunger engagement portion, and wherein the spring engages an inner wall at a distal end of the plunger engagement portion.

7. The apparatus of claim 6, wherein an outer wall at the distal end of the plunger engagement portion engages the plunger.

8. The apparatus of claim 6, wherein the actuator rod extends into the plunger engagement portion, wherein a portion of the actuator rod that extends within the plunger engagement portion includes a radially extending flange, and wherein the clutch connects a proximal face of the flange to the inner wall at the proximal end of the plunger engagement portion.

9. The apparatus of claim 6, wherein the clutch disengages the distal end of the actuator rod from the plunger engagement section in response to a compression of the spring.

10. The apparatus of claim 9, wherein the spring compresses in response to a plunger reaction force applied by the plunger of the syringe to the plunger engagement portion.

11. The apparatus of claim 1, wherein the distal end of the body is configured to connect to the syringe, and wherein the plunger of the syringe extends within the body.

12. An apparatus for controlling a plunger of a syringe for delivering a fluid from an interior of the syringe, the apparatus comprising:
a handle and a cooperating trigger, wherein the trigger comprises a first portion connected to a second portion by a joint; and
a spring connecting the first portion to the second portion, wherein the first portion of the trigger is configured to engage the plunger of the syringe and receive a plunger reaction force applied by the plunger of the syringe, wherein movement of the second portion of the trigger toward the handle applies a stretching force to the spring in response to the plunger reaction force, and wherein the first portion of the trigger disengages the plunger of the syringe in response to the stretching force greater than a threshold force applied to the spring.

13. The apparatus of claim 12, wherein the handle and the cooperating trigger operate one of a spring biased grip drive and a ratchet driven grip drive.

14. The apparatus of claim 12, wherein the first portion of the trigger engages the plunger of the syringe via at least one of a piston and a drive grip, and wherein the first portion of the trigger breaks the engagement with the at least one of the piston and the drive grip in response to the stretching force greater than the threshold force applied to the spring.

15. An apparatus for controlling a plunger of a syringe for delivering a fluid from an interior of the syringe, the apparatus comprising:
an actuator rod extending from a proximal end to a distal end;
a spring extending within the actuator rod, wherein a distal end of the spring is configured to engage the plunger of the syringe; and
a body having a proximal end, a distal end, and an opening at the proximal end, wherein the opening receives the distal end of the actuator rod, and wherein the actuator rod comprises at least one indicator that indicates a desired amount of compression of the spring.

16. The apparatus of claim 15, wherein an outer wall of the actuator rod is in ratcheting engagement with an inner wall of the body.

17. The apparatus of claim 16, wherein a distal end of the actuator rod comprises a radially extending pawl, and wherein the inner wall of the body comprises a plurality of teeth.

18. The apparatus of claim 15, wherein at least a portion of the actuator rod and at least a portion of the body are transparent such that the spring and the plunger are visible through the actuator rod and the body.

19. The apparatus of claim 18, wherein a location of the at least one indicator with respect to a location of at least one of the distal end of the spring and a proximal end of the plunger indicates the desired amount of compression of the spring.

20. The apparatus of claim 19, wherein the actuator rod comprises at least two indicators spaced apart from one another, and wherein a location of the at least one of the distal end of the spring and the proximal end of the plunger between the at least two indicators indicates the desired amount of compression of the spring.

21. The apparatus of claim 15, wherein the distal end of the body is configured to connect to the syringe, wherein the plunger of the syringe extends within the body.

* * * * *